United States Patent
Gatto

(10) Patent No.: US 9,994,531 B2
(45) Date of Patent: *Jun. 12, 2018

(54) ANTIOXIDANT COMPOSITIONS AND LUBRICATING COMPOSITIONS CONTAINING THE SAME

(71) Applicant: VANDERBILT CHEMICALS, LLC, Norwalk, CT (US)

(72) Inventor: Vincent J. Gatto, Bradenton, FL (US)

(73) Assignee: VANDERBILT CHEMICALS, LLC, Norwalk, CT (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/226,316

(22) Filed: Aug. 2, 2016

(65) Prior Publication Data

US 2017/0044455 A1 Feb. 16, 2017

Related U.S. Application Data

(60) Provisional application No. 62/205,250, filed on Aug. 14, 2015.

(51) Int. Cl.
| | |
|---|---|
| *C10M 169/04* | (2006.01) |
| *C07D 249/08* | (2006.01) |
| *C10M 133/44* | (2006.01) |
| *C10N 30/10* | (2006.01) |

(52) U.S. Cl.
CPC ......... *C07D 249/08* (2013.01); *C10M 133/44* (2013.01); *C10M 169/04* (2013.01); *C10M 2203/1006* (2013.01); *C10M 2215/22* (2013.01); *C10M 2215/223* (2013.01); *C10M 2215/30* (2013.01); *C10M 2219/066* (2013.01); *C10N 2030/10* (2013.01); *C10N 2230/10* (2013.01)

(58) Field of Classification Search
CPC .............. C10M 133/44; C10M 169/04; C10M 2215/22; C10M 2215/223; C10M 2203/1006; C10M 2219/066; C10M /; C10N 2230/10

See application file for complete search history.

(56) References Cited

U.S. PATENT DOCUMENTS

| | | | |
|---|---|---|---|
| 4,734,209 | A | 3/1988 | Phillips et al. |
| 4,880,551 | A | 11/1989 | Doe |
| 5,580,482 | A | 12/1996 | Chasan et al. |
| 6,121,209 | A | 9/2000 | Watts et al. |
| 6,184,262 | B1 | 2/2001 | Suhoza et al. |
| 6,410,490 | B1 | 6/2002 | Reyes-Gavilan et al. |
| 6,743,759 | B2 | 6/2004 | Stunkel et al. |
| 2003/0134753 | A1* | 7/2003 | Stunkel ............... C09K 15/30 508/281 |

(Continued)

OTHER PUBLICATIONS

International Search Report dated Sep. 21, 2016, dated Oct. 7, 2016.

*Primary Examiner* — Taiwo Oladapo
(74) *Attorney, Agent, or Firm* — Norris McLaughlin & Marcus LLP

(57) ABSTRACT

An antioxidant composition which comprises:
(a) methylenebis(di-n-butyldithiocarbamate); and
(b) an alkylated diphenylamine derivative of triazole wherein the alkyl group on at least one of the phenyl groups is $C_8$ or higher.

Lubricating compositions containing the antioxidant composition are also contemplated.

4 Claims, 3 Drawing Sheets

(56) References Cited

U.S. PATENT DOCUMENTS

| | | |
|---|---|---|
| 2004/0038835 A1 | 2/2004 | Chasan et al. |
| 2008/0200357 A1 | 8/2008 | Chasan et al. |
| 2010/0173808 A1 | 7/2010 | Chasan et al. |
| 2016/0068781 A1 | 3/2016 | Yao et al. |

* cited by examiner

ANTIOXIDANT COMPOSITIONS AND LUBRICATING COMPOSITIONS CONTAINING THE SAME

FIELD OF THE INVENTION

The invention relates to improved antioxidant compositions containing (a) methylenebis(di-n-butyl-dithiocarbamate) and (b) alkylated diphenylamine derivatives of triazole wherein the alkyl group on at least one of the phenyl groups is $C_8$ or higher; and lubricating compositions containing the same.

BACKGROUND OF THE INVENTION

In U.S. Pat. No. 4,880,551, there are provided synergistic antioxidant compositions containing (a) 1-[di(4-octylphenyl)aminomethyl]tolutriazole and (b) an antioxidant selected from the group consisting of methylenebis(di-n-butyldithiocarbamate), 2,6-di-t-butyl-4-sec-butylphenol, 2,6-di-t-butyl-4-methylphenol and butylated phenol mixture and wherein the ratio of the tolutriazole compound to the antioxidant ranges from about 1:4 to about 4:1.

In U.S. Pat. No. 6,743,759, there are provided improved antioxidant, antiwear/extreme pressure additive compositions containing (a) methylenebis(di-n-butyldithiocarbamate) and (b) a diphenylamine derivative of tolutriazole or benzotriazole wherein the (a):(b) mass percent ratio ranges from above about 4:1 to about 50:1 and lubricating compositions containing the same.

U.S. Applications 20100173808, 20080200357 and 20040038835 and U.S. Pat. Nos. 4,734,209, 5,580,482 and 6,410,490 describe derivatized triazoles, including a $C_7$-$C_{13}$ aralkyl derivative (equivalent to di-$C_1$-$C_7$ alkylated diphenylamine) but do not specifically reference di-octyldiphenylamine (or higher) derivatives of triazole and do not teach the use of methylenebis(di-n-butyldithiocarbamate). In addition, these references do not show any examples of the preparation or application of diphenylamine derivatives of triazole.

U.S. Patent Application 2016/0068781 describes combinations of alkylated phenyl-alpha-naphthylamine ("APANA"), alkylated diphenylamine derivatives of tolutriazole, and methylenebis(di-n-butyldithiocarbamate). While that reference also suggests alkylated diphenylamine derivatives of triazole, there is no discussion of such compounds having alkyl groups being $C_8$ or higher; and no suggestion that by using such $C_8$ or higher alkylated diphenylamine derivatives of triazole in combination with methylenebis(di-n-butyldithiocarbamate), excellent results can be achieved without the presence of the required APANA. Thus, the present invention covers an additive combination or lubricating composition comprising the additive composition comprising $C_8$ or higher alkylated diphenylamine derivatives of triazole in combination with methylenebis(di-n-butyldithiocarbamate), in which said composition is free or substantially free of APANA.

It has been discovered that methylenebis(di-n-butyldithiocarbamate) when used in conjunction with an alkylated diphenylamine derivative of a 1,2,4-triazole (henceforth "triazole derivative"), at a ratio of above about 1:2 to about 50:1, shows a significant synergistic effect with improved antioxidant performance in lubricants over that which is observed with a diphenylamine derivative of benzotriazole or tolutriazole.

SUMMARY OF THE INVENTION

One embodiment of the invention is an antioxidant composition with improved antioxidant performance which comprises: (a) methylenebis(di-n-butyldithiocarbamate) and (b) alkylated diphenylamine derivatives of triazole wherein the alkyl group on at least one of the phenyl groups is $C_8$ or higher, and wherein the (a):(b) mass percent ratio ranges from above about 1:2 to about 50:1, preferably about 1:1 to about 40:1, and more preferably about 1:1 to about 20:1.

A further embodiment of the invention relates lubricating compositions having improved antioxidant properties which comprise a major portion of an oil of lubrication viscosity (at least about 90%, and preferably at least about 95% by weight) and an oxidation inhibiting amount of the antioxidant composition of the invention, at about 0.001-5%, preferably about 0.1-3%, more preferably about 0.5-0.75% by weight of the total lubricating composition. It is noted that where component (b) is added as diluted in process oil, the weight of (b) is set forth only with respect to the active portion of the triazole derivative, i.e. not counting the weight of the process oil.

DETAILED DESCRIPTION OF THE INVENTION

Figure 1:
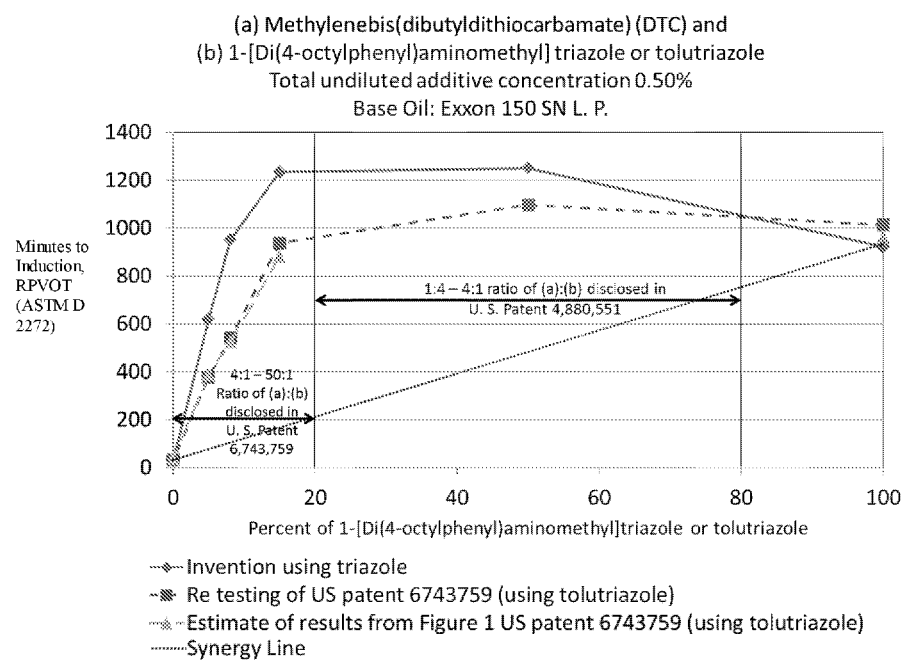
FIG. 1 depicts the number of minutes to induction (based on RPVOT (ASTM D2272 test)) for various ratios of (a):(b) where (a) is methylenebis-(dibutyldithiocarbamate) and (b) 1-[di-(4-octylphenyl)aminomethyl]tolutriazole or 1-[di-(4-octylphenyl)aminomethyl]triazole.

Compound A (Methylenebis(di-n-butyldithiocarbamate): Methylenebis(di-n-butyldithiocarbamate) is a known material and is commercially available under the trade name VANLUBE® 7723, and is distributed by Vanderbilt Chemicals, LLC. Small amounts of the tolutriazole derivative produces synergistic antioxidant effects when combined with methylenebis(di-n-butyldithiocarbamate) in certain ratios as was shown in U.S. Pat. No. 4,880,551. Surprisingly, it has been discovered that improved antioxidant properties can be achieved in lubricant formulations by replacing the benzotriazole or tolutriazole in U.S. Pat. Nos. 4,880,551 and 6,743,759 with alkylated diphenylamine derivative of 1,2,4-triazole and that a ratio of above about 1:2 to 50:1 (by weight) of methylenebis(di-n-butyldithiocarbamate):triazole derivative is particularly effective, even without the presence of APANA.

Compound B (alkylated diphenylamine derivatives of triazole): The 1-[alkyl diphenyl)aminomethyl]triazole compounds are prepared from 1,2,4-triazole (triazole), a formaldehyde source and alkylated diphenylamine by means of the Mannich reaction. These reactions are described in U.S. Pat. No. 4,734,209 where the alkylated diphenylamine is replaced by various secondary amines, and in U.S. Pat. No. 6,184,262, where the triazole is replaced by benzotriazole or tolutriazole. Water is a by-product of the reaction. The reaction may be carried out in a volatile organic solvent, in a diluent oil or in the absence of a diluent. When a volatile organic solvent is used, in general the solvent is removed by distillation after the reaction is complete. A slight stoichiometric excess of either the 1,2,4-triazole, the formaldehyde source, or the alkylated diphenylamine may be used without adversely affecting the utility of the final product isolated. The triazole derivatives are of general formula I

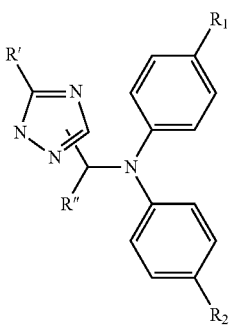

(I)

wherein R' and R" are independently selected from hydrogen or lower alkyl, R1 and R2 are independently selected from alkyl having up to 12 carbon atoms or phenylalkyl, or mixtures thereof. The triazole derivatives of formula I may also be represented by the following discrete chemical structures where each possible isomer are described:

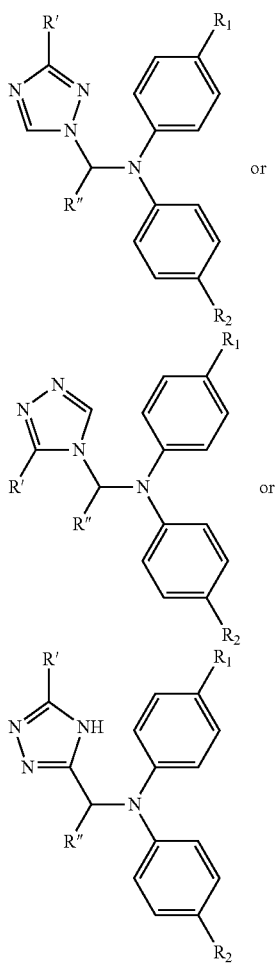

It is understood that in preparing these alkylated diphenylamine derivatives of triazole, many possible isomers of the derivatives are possible. Below are other ways of possibly naming these molecules where R' and R" are hydrogen, and R1 and R2 are alkyl:

1H-1,2,4-triazole-1-methanamine, N,N-bis(4-alkylphenyl)-
N,N-bis(4-alkylphenyl)-((1,2,4-triazol-1-yl)methyl)amine
N,N-bis(4-alkylphenyl)aminomethyl-1,2,4-triazole
N,N-bis(4-alkylphenyl)-((1,2,4-triazole-1-yl)methyl)amine
Bis(4-alkylphenyl)(1H-1,2,4-triazol-1-ylmethyl)amine
N,N-bis(4-alkylphenyl)-1H[(1,2,4-triazol-1-yl)methyl] amine
N,N-bis(4-alkylphenyl)-[(1,2,4-triazol-1-yl)methyl]amine
N,N-bis(4-alkylphenyl)-1,2,4-triazole-1-ylmethanamine The alkylated diphenylamine portion of the triazole derivatives may be propylated, butylated, pentylated, hexylated, heptylated, octylated, nonylated, decylated, undecylated, dodecylated, tridecylated, tetradecylated, pentadecylated, hexadecylated). The alkyl groups may be linear, branched or cyclic in nature. Preferably, the alkylated diphenylamine portion of the triazole derivative is butylated, octylated or nonylated. Examples include:

1-[(4-butylphenyl)(phenyl)aminomethyl]triazole
1-[(4-octylphenyl)(phenyl)aminomethyl]triazole
1-[di-(4-butylphenyl)aminomethyl]triazole
1-[di-(4-octylphenyl)aminomethyl]triazole
1-[(4-nonylphenyl)(phenyl)aminomethyl]triazole
1-[di-(4-nonylphenyl)aminomethyl]triazole
1-[(4-butylphenyl)(4-octylphenyl)aminomethyl]triazole Also contemplated is a mixture of molecules described as 1-[di-(4-mixed butyl/octylphenyl)aminomethyl]triazole, which comprises a mixture of 1-[(4-butylphenyl)(phenyl) aminomethyl]triazole, 1-[(4-octylphenyl)(phenyl) aminomethyl]triazole, 1-[di-(4-butylphenyl)aminomethyl]triazole, 1-[di-(4-octylphenyl)aminomethyl]triazole, and 1-[(4-butylphenyl) (4-octylphenyl) aminomethyl]triazole.

One key advantage of the octylated and nonylated diphenylamine derivatives of triazole is in their method of preparation. Both the octylated and nonylated diphenylamine derivatives of triazole are prepared from their corresponding alkylated diphenylamines. In the case of the octylated and nonylated diphenylamines, they are easily prepared from refluxing octenes and nonenes in high yield and purity. However, the heptylated diphenylamine, under the same conditions of refluxing olefin, cannot be prepared in either high yield or high purity. This is clearly illustrated in the experimental section where the preparation of the octylated diphenylamine is compared to the preparation of heptylated diphenylamine. For example, the 1-octene reaction in Example B herein shows complete reaction of diphenylamine in 15 hours and produces a product with no unreacted diphenylamine. However, the 1-heptene reaction in Example D has 57% unreacted diphenylamine after 25 hours and produces a product contaminated with 50% unreacted diphenylamine.

The ability to more easily produce C8 or higher alkylated diphenylamines provides significant advantages in the C8 or higher alkylated diphenylamine derivatives of triazole. First, higher molecular weight products can be produced. This provides significant benefits from a toxicological and environmental standpoint. Second, less volatile products are produced which allow for expanded utility in today's higher quality and more demanding lubricants. In fact, the change in volatility in moving from a C7 based alkylated diphenylamine to a C8 and higher based alkylated diphenylamine, or in moving from a C7 based alkylated diphenylamine derivative of triazole to a C8 and higher based alkylated diphenylamine derivative of triazole, is striking. As the volatility examples illustrate, there is a marked reduction in volatility when one moves from C7 based products to C8 based products. This is due to two factors, (1) the higher molecular weight of the C8 and higher products, and (2) the greater ease of preparation of highly alkylated C8 and higher products.

An advantage of the alkylated diphenylamine derivatives of triazole over the alkylated diphenylamine derivatives of tolutriazole or benzotriazole is their physical form and solubility. It is well known that alkylated diphenylamine derivatives of tolutriazole must be diluted in solvent in order to produce an easily handled liquid. Furthermore, such dilutions of alkylated diphenylamine derivatives of tolutriazole are known to form a substantial amount of crystals on standing for short periods of time which significantly complicate their handling and application in finished lubricants. This crystallization can also result in quality issues in products where such a crystallized material is used. Generally, this issue can be resolved by heating. However, heating adds a complication to the formulation process and can be costly and time consuming. Also, if done improperly, heating can result in decomposition of the partially crystallized product. Thus the improved solubility and fully liquid physical form of the alkylated diphenylamine derivatives of triazole provide a substantial handling, processing and quality benefit for lubricant package and finished fluid formulators.

The improved compositions of the invention of (a) methylenebis(di-n-butyldithiocarbamate) and (b) $C_8$ or higher alkylated diphenylamine derivatives of triazole may be incorporated in the lubricating compositions by known methods in an amount effective to produce the desired oxidation inhibiting characteristics. In one embodiment of the invention, the total additive amount (a)+(b) may range from about 0.005 to 5.0 percent by weight based on the total weight of the lubricating composition. In another embodiment of the invention, the amount range is about 0.01 to 3.0 percent, more preferably about 0.1 to 1.0 percent of the additive based on the total weight of the lubricating composition. The compositions impart metal deactivating as well as oxidation inhibiting properties to natural and synthetic lubricants formulated as oils or greases. With respect to the additive ratio in a stand-alone additive composition, or as part of an overall lubricating composition, the additive comprising (a) methylenebis(di-n-butyldithiocarbamate) and (b) $C_8$ or higher alkylated diphenylamine derivatives of triazole, may be present wherein the (a):(b) mass ratio ranges about 1:2 to about 50:1, preferably about 1:2 to about 10:1, more preferably about 1:1 to about 40:1, and most preferably about 2:1 to about 38:1.

The lubricating oils are typical formulated oils used in automotive and industrial applications such as, among others, greases, metalworking fluids, heat transfer oils, turbine oils, compressor oils, transformer oils, hydraulic oils, gear oils, transmission fluids, spark ignited (gasoline) engine oils and compression ignited (diesel) engine oils. Natural base oils used to formulate the lubricating oils include mineral oils, petroleum oils, and vegetable oils. The base oil may also be selected from oils derived from petroleum hydrocarbon and synthetic sources. The hydrocarbon base oil may be selected from naphthenic, aromatic, and paraffinic mineral oils. The synthetic oils may be selected from, among others, ester-type oils (such as silicate esters, pentaerythritol esters and carboxylic acid esters), hydrogenated mineral oils, silicones, silanes, polysiloxanes, alkylene polymers, and polyglycol ethers.

The lubricating compositions optionally contain the necessary ingredients to prepare the composition, as for example dispersing agents, emulsifiers, and viscosity improvers. Greases may be prepared by adding thickeners, as for example salts and complexes of fatty acids, polyurea compounds, clays and quarternary ammonium bentonite. Depending on the intended use of the lubricant, other functional additives may be added to enhance a particular property of the lubricant.

The lubricating compositions may also contain one or more of the following additives:
1. Borated and/or non-borated ashless dispersants
2. Additional antioxidant compounds
3. Seal swell compositions
4. Organic and organo-metallic friction modifiers
5. Extreme pressure/antiwear agents
6. Viscosity modifiers
7. Pour point depressants
8. Metallic detergents
9. Phosphates
10. Antifoamants
11. Rust inhibitors
12. Copper corrosion inhibitors 1. Borated and/or Non-Borated Dispersants Non-borated ashless dispersants may be incorporated within the final fluid composition in an amount comprising up to 10 weight percent on an oil-free basis. Many types of ashless dispersants listed below are known in the art. Borated ashless dispersants may also be included.

(A) "Carboxylic dispersants" are reaction products of carboxylic acylating agents (acids, anhydrides, esters, etc.) containing at least about 34 and preferably at least about 54 carbon atoms reacted with nitrogen-containing compounds (such as amines), organic hydroxy compounds (such aliphatic compounds including monohydric and polyhydric alcohols, or aromatic compounds including phenols and naphthols), and/or basic inorganic materials. Examples of these "carboxylic dispersants" are described in British Patent 1,306,529 and in U.S. Pat. Nos. 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, and Re 26,433, which are incorporated herein by reference for disclosure of carboxylic dispersants.

(B) "Amine dispersants" are reaction products of relatively high molecular weight aliphatic or alicyclic halides and amines, preferably polyalkylene polyamines. Examples thereof are described, for example, in U.S. Pat. Nos. 3,275,554, 3,438,757, 3,454,555, and 3,565,804 which are incorporated herein by reference for disclosure of amine dispersants.

(C) "Mannich dispersants" are the reaction products of alkyl phenols in which the alkyl group contains at least about 30 carbon atoms with aldehydes (especially formaldehyde) and amines (especially polyalkylene polyamines). The materials described in U.S. Pat. Nos. 3,036,003, 3,236,770, 3,414,347, 3,448,047, 3,539,633, 3,586,629, 3,591,598, 3,634,515, 3,725,480, and 3,726,882 are incorporated herein by reference for disclosure of Mannich dispersants.

(D) Post-treated dispersants are obtained by reacting carboxylic, amine or Mannich dispersants with reagents such as urea, thiourea, carbon disulfide, aldehydes, ketones, carboxylic acids, hydrocarbon-substituted succinic anhydrides, nitriles, epoxides, boron compounds, phosphorus compounds or the like. U.S. Pat. Nos. 3,200,107, 3,282,955, 3,367,943, 3,513,093, 3,639,242, 3,649,659, 3,442,808, 3,455,832, 3,579,450, 3,600,372, 3,702,757, and 3,708,422 are incorporated herein by reference for disclosure of post-treated dispersants.

(E) Polymeric dispersants are interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. Polymeric dispersants are disclosed in U.S. Pat. Nos. 3,329,658, 3,449,250, 3,519,656, 3,666,730, 3,687,849, and 3,702,300 which are incorporated herein by reference for disclosure of polymeric dispersants.

Borated dispersants are described in U.S. Pat. Nos. 3,087,936 and 3,254,025 which are incorporated herein by reference for disclosure of borated dispersants.

Also included as possible dispersant additives are those disclosed in U.S. Pat. Nos. 5,198,133 and 4,857,214 which are incorporated herein by reference. The dispersants of these patents compare the reaction products of an alkenyl succinimide or succinimide ashless dispersant with a phosphorus ester or with an inorganic phosphorus-containing acid or anhydride and a boron compound.

2. Additional Antioxidant Compounds

Other antioxidants may be used in the compositions of the present invention, if desired. Typical antioxidants include hindered phenolic antioxidants, secondary aromatic amine antioxidants, sulfurized phenolic antioxidants, oil-soluble copper compounds, organo-molybdenum compounds, phosphorus-containing antioxidants, organic sulfides, disulfides and polysulfides and the like.

Illustrative examples of sterically hindered phenolic antioxidants include ortho-alkylated phenolic compounds such as 2,6-di-tert-butylphenol, 4-methyl-2,6-di-tert-butylphenol, 2,4,6-tri-tert-butylphenol, 4-(N,N-dimethylaminomethyl)-2,6-di-tert-butylphenol, 4-ethyl-2,6-di-tertbutylphenol, 2,6-distyryl-4-nonylphenol, 1,6-hexamethylene-bis(3,5-di-tert-butyl-4-hydroxyhydrocinnamate), 3,5-di-tert-butyl-4-hydroxyhydrocinnamic acid, $C_{10}$-$C_{14}$ alkyl esters, 3,5-di-tert-butyl-4-hydroxyhydrocinnamic acid, $C_7$-$C_9$ alkyl esters, 3,5-di-tert-butyl-4-hydroxyhydrocinnamic acid, iso-octyl ester, 3,5-di-tert-butyl-4-hydroxyhydrocinnamic acid, butyl ester, 3,5-di-tert-butyl-hydroxyhydrocinnamic acid, methyl ester, tetrakis-(3-(3,5-di-tert-butyl-4-hydroxyphenyl)-propionyloxymethyl)methane, thiodiethylene bis(3,5-di-tert-butyl-4-hydroxyhydrocinnamate), octadecyl 3,5-di-tert-butyl-4-hydroxyhydrocinnamate, N,N'-bis(3,5-di-tert-butyl-4-hydroxyphenylpropionyl)hexamethylene diamine, N,N'-bis(3,5-di-tert-butyl-4-hydroxyphenylpropionyl)trimethylene diamine, N,N'-bis(3,5-di-tert-butyl-4-hydroxyphenylpropionyl) hydrazine and their analogs and homologs. Mixtures of two or more such hindered phenolic compounds are also suitable.

Other preferred hindered phenol antioxidants for use in the compositions of this invention are methylene-bridged alkylphenols, and these can be used singly or in combinations with each other, or in combinations with sterically-hindered unbridged phenolic compounds. Illustrative methylene-bridged compounds include 4,4'-methylenebis(6-tert-butyl-o-cresol), 4,4'-methylenebis(2-tert-amyl-o-cresol), 2,2'-methylenebis(4-methyl-6-tert-butylphenol), 4,4'-methylenebis(2,6-di-tert-butylphenol), and similar compounds. Particularly preferred are mixtures of methylene-bridged alkylphenols such as are described in U.S. Pat. No. 3,211,652, which is incorporated herein by reference.

Amine antioxidants, especially oil-soluble aromatic secondary amines may also be used in the compositions of this invention. Although aromatic secondary monoamines are preferred, aromatic secondary polyamines are also suitable. Illustrative aromatic secondary monoamines include diphenylamine, alkyl diphenylamines containing 1 or 2 alkyl substituents each having up to about 16 carbon atoms, phenyl-β-naphthylamine, and phenyl-α-napthylamine.

A preferred type of aromatic amine antioxidant is an alkylated diphenylamine of the general formula:

$$R_1\text{—}C_6H_4\text{—}NH\text{—}C_6H_4\text{—}R_2$$

where $R_1$ is an alkyl group (preferably a branched alkyl group) having 4 to 12 carbon atoms, (more preferably 8 or 9 carbon atoms) and $R_2$ is a hydrogen atom or an alkyl group (preferably a branched alkyl group) having 4 to 12 carbon atoms, (more preferably 8 or 9 carbon atoms). Most preferably, $R_1$ and $R_2$ are the same. One such preferred compound is available commercially as NAUGALUBE® 438L, a material which is understood to be predominately a 4,4'-dinonyldiphenylamine (i.e., bis(4-nonylphenyl) (amine)) in which the nonyl groups are branched. Another such preferred compound is available commercially as VANLUBE® 961 or IRGANOX® L57, a material which is understood to be a mixture of butylated and octylated alkylated diphenylamines.

Another useful type of antioxidant are 2,2,4-trimethyl-1,2-dihydroquinoline (TMDQ) polymers and homologs containing aromatized terminal units such as those described in U.S. Pat. No. 6,235,686, which is hereby incorporated by reference.

Mixtures of different antioxidants may also be used.

3. Seal Swell Compositions

Compositions which are designed to keep seals pliable are also well known in the art. A preferred seal swell composition is isodecyl sulfolane. The seal swell agent is preferably incorporated into the composition at about 0.1-3 weight percent. Substituted 3-alkoxysulfolanes are disclosed in U.S. Pat. No. 4,029,587 which is incorporated herein by reference.

4. Friction Modifiers

Friction modifiers are also well known to those skilled in the art. A useful list of friction modifiers are included in U.S. Pat. No. 4,792,410, which is incorporated herein by reference. U.S. Pat. No. 5,110,488 discloses metal salts of fatty acids and especially zinc salts and is incorporated herein by reference. Useful friction modifiers include fatty phosphites, fatty acid amides, fatty epoxides, borated fatty epoxides, fatty amines, glycerol esters, borated glycerol esters alkoxylated fatty amines, borated alkoxylated fatty amines, metal salts of fatty acids, sulfurized olefins, fatty imidazolines, molybdenum dithiocarbamates (e.g., U.S. Pat. No. 4,259,254, incorporated herein by reference), molybdate esters (e.g., U.S. Pat. Nos. 5,137,647 and 4,889,647, both incorporated herein by reference), molybdate amine with sulfur donors (e.g., U.S. Pat. No. 4,164,473 incorporated herein by reference), and mixtures thereof.

The preferred friction modifier is a borated fatty epoxide as previously mentioned as being included for its boron content. Friction modifiers are preferably included in the compositions in the amounts of 0.1-10 weight percent and may be a single friction modifier or mixtures of two or more.

5. Extreme Pressure/Antiwear Agents

Dialkyl dithiophosphate succinates may be added to provide antiwear protection. Zinc salts are preferably added as zinc salts of phosphorodithioic acids or dithiocarbamic acid. Among the preferred compounds for use are zinc, diisooctyl dithiophosphate and zinc dibenzyl dithiophosphate and amyl dithiocarbamic acid. Also included in lubricating compositions in the same weight percent range as the zinc salts to give antiwear/extreme pressure performance are dibutyl hydrogen phosphite (DBPH) and triphenyl monothiophosphate, and the thiocarbamate ester formed by reacting dibutyl amine-carbon disulfide- and the methyl ester of acrylic acid. The thiocarbamate is described in U.S. Pat. No. 4,758, 362 and the phosphorus-containing metal salts are described in U.S. Pat. No. 4,466,894. Both patents are incorporated herein by reference. Antimony or lead salts may also be used for extreme pressure. The preferred salts are of dithiocarbamic acid such as antimony diamyldithiocarbamate. Examples of commercial anti-wear and Extreme Pressure agents that may be used include VANLUBE® 727, VANLUBE® 7611M, VANLUBE® 9123, VANLUBE® 871 and VANLUBE® 981 all manufactured by Vanderbilt Chemicals, LLC. Triaryl phosphates may also be used as antiwear additives and include triphenyl phosphate, tricresol phosphate and tri-butylated phenyl phosphate.

6. Viscosity Modifiers

Viscosity modifiers (VM) and dispersant viscosity modifiers (DVM) are well known. Examples of VMs and DVMs are polymethacrylates, polyacrylates, polyolefins, styrene-maleic ester copolymers, and similar polymeric substances including homopolymers, copolymers and graft copolymers. Summaries of viscosity modifiers can be found in U.S. Pat. Nos. 5,157,088, 5,256,752 and 5,395,539, which are incorporated herein by reference. The VMs and/or DVMs preferably are incorporated into the fully-formulated compositions at a level of up to 10% by weight.

7. Pour Point Depressants (PPD)

These components are particularly useful to improve low temperature qualities of lubricating oil. A preferred pour point depressant is an alkylnaphthalene. Pour point depressants are disclosed in U.S. Pat. Nos. 4,880,553 and 4,753,745, which are incorporated herein by reference. PPDs are commonly applied to lubricating compositions to reduce viscosity measured at low temperatures and low rates of shear. The pour point depressants are preferably used in the range of 0.1-5 weight percent.

8. Detergents

Lubricating compositions in many cases also preferably include detergents. Detergents as used herein are preferably metal salts of organic acids. The organic acid portion of the detergent is preferably a sulphonate, carboxylate, phenate, or salicylate. The metal portion of the detergent is preferably an alkali or alkaline earth metal. Preferred metals are sodium, calcium, potassium and magnesium. Preferably, the detergents are overbased, meaning that there is a stoichiometric excess of metal over that needed to form the neutral metal salt.

Preferred overbased organic salts are the sulfonate salts having a substantially oleophilic character and which are formed from organic materials. Organic sulfonates are well known materials in the lubricant and detergent arts. The sulfonate compound should preferably contain on average from about 10 to about 40 carbon atoms, more preferably from about 12 to about 36 carbon atoms and most preferably from about 14 to about 32 carton atoms on average. Similarly, the phenates, oxylates and carboxylates preferably have a substantially oleophilic character.

Examples of detergents can be found in U.S. Pat. Nos. 2,228,654, 2,250,188, 2,252,663, 2,865,956, 3,150,089, 3,256,186 and 3,410,798 which are incorporated herein by reference. The amount of the overbased salt utilized in the composition is preferably from about 0.1 to about 10 weight percent on an oil free basis. The overbased salt is usually made up in about 50% oil with a TBN range of 10-600 on an oil free basis. Borated and non-borated overbased detergents are described in U.S. Pat. Nos. 5,403,501 and 4,792,410 which are herein incorporated by reference for disclosure pertinent hereto.

9. Phosphates

The lubricating compositions can also preferably include at least one phosphorus acid, phosphorus acid salt, phosphorus acid ester or derivative thereof including sulfur-containing analogs preferably in the amount of 0.002-1.0 weight percent. The phosphorus acids, salts, esters or derivatives thereof include compounds selected from phosphorus acid esters or salts thereof, phosphites, phosphorus-containing amides, phosphorus-containing carboxylic acids or esters, phosphorus containing ethers and mixtures thereof In one embodiment, the phosphorus acid, ester or derivative can be a phosphorus acid, phosphorus acid ester, phosphorus acid salt, or derivative thereof. The phosphorus acids include the phosphoric, phosphonic, phosphinic, and thio-phosphoric acids including dithiophosphoric acid as well as the monothiophosphoric, thiophosphinic and thiophosphonic acids.

One class of compounds are adducts of O,O-dialkyl-phosphorodithioates and esters of maleic or fumaric acid. The compounds can be prepared by known methods as described in U.S. Pat. No. 3,359,203, as for example O,O-di(2-ethylhexyl) S-(1,2-dicarbobutoxyethyl)phosphorodithioate.

Another class of compounds useful to the invention are dithiophosphoric acid esters of carboxylic acid esters. Preferred are alkyl esters having 2 to 8 carbon atoms, as for example 3-[[bis(1-methylethoxy)phosphinothioyl]thio]propionic acid ethyl ester.

A third class of ashless dithiophosphates for use with the present invention include:
(i) those of the formula

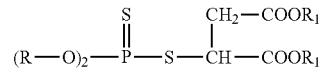

wherein R and R$_1$ are independently selected from alkyl groups having 3 to 8 carbon atoms (commercially available as VANLUBE 7611M, from Vanderbilt Chemicals, LLC);
(ii) dithiophosphoric acid esters of carboxylic acid such as those commercially available as IRGALUBE® 63 from BASF Corp.;
(iii) triphenylphosphorothionates such as those commercially available as IRGALUBE® TPPT from BASF Corp.; and 10. Antifoamants Antifoaming agents are well-known in the art as silicone or fluorosilicone compositions. Such antifoam agents are available from Dow Corning Corporation and Union Carbide Corporation. A preferred fluorosilicone antifoam product is Dow FS-1265. Preferred silicone antifoam products are Dow Corning DC-200 and Union Carbide UC-L45. Also, a siloxane polyether copolymer antifoamer available from OSI Specialties, Inc. of Farmington Hills, Mich. may also be included. One such material is sold as SILWET-L-7220. The antifoam products are preferably included in the compositions of this invention at a level of 5 to 80 parts per million with the active ingredient being on an oil-free basis.

11. Rust Inhibitors

Embodiments of rust inhibitors include metal salts of alkylnaphthalenesulfonic acids.

12. Copper Corrosion Inhibitors

Embodiments of copper corrosion inhibitors which may optionally be added include thiazoles, triazoles and thiadiazoles. Example embodiments of such compounds include benzotriazole, tolyltriazole, octyltriazole, decyltriazole, dodecyltriazole, 2-mercapto benzothiazole, 2,5-dimercapto- 1,3,4-thiadiazole, 2-mercapto-5-hydrocarbylthio-1,3,4-thiadiazoles, 2-mercapto-5-hydrocarbyldithio-1,3,4-thiadiazoles, 2,5-bis(hydrocarbylthio)-1,3,4-thiadiazoles, and 2,5-bis(hydrocarbyldithio)-1,3,4-thiadiazoles.

The following examples are given for the purpose of illustrating the invention and are not intended to limit the invention. All percentages and parts are based on weight unless otherwise indicated.

EXAMPLES

Experimental

Preparation of Alkylated Diphenylamines

Example A: alkylation of diphenylamine with 1-octene using Fulcat 220 catalyst 22% by weight. In a 500 mL four-necked round bottom flask equipped with a temperature probe, addition funnel, Dean Stark set up with reflux condenser and overhead stirrer were charged diphenylamine (100 g, 0.585 mole) and clay catalyst Fulcat 220 (15 g). Reaction mixture was rapidly mixed and heated to 130-135° C. under nitrogen. 1-Octene (193 g, 1.685 mole) was added dropwise at 135° C. for two hours. After addition of 1-octene, the reaction mixture was continued stirring at 135-140° C. for 12 h. More Fulcat catalyst (7.5 g) was added and continued heating at 135° C. for another 14 h. Periodically, 1 mL reaction samples were taken for GCMS to check the progress of the reaction. After 26 h, the reaction mixture was cooled to room temperature and filtered. The filtrate was distilled using water aspirator vacuum to remove excess alkene. An amber oil (158.85 g) was isolated. GCMS analysis of the various reaction mixtures and final product are provided in Table 1. As the table indicates, all the diphenylamine was reacted after 22 hours and the amber oil product was composed of 68.48% mono-linear octylated diphenylamine and 31.54% di-linear octylated diphenylamine. This is a desirable product for preparation of triazole derivatives because there is no unreacted diphenylamine in the product.

Example A GCMS timed data: alkylation using fulcat 220, 22% by weight

TABLE 1

| | Time h | | | | | | | | | |
|---|---|---|---|---|---|---|---|---|---|---|
| Chemical | 2 | 4 | 8 | 12 | 16 | 20 | 22 | 24 | 26 | dist |
| 1-octene | 40.79 | 36.22 | 26.07 | 14.01 | 24.44 | 10.73 | 10.72 | 3.64 | 1.56 | 0 |
| DPA | 30.49 | 19.53 | 8.42 | 4.81 | 1.02 | 0.24 | 0 | 0 | 0 | 0 |
| Total Mono alkyl | 19.26 | 30.08 | 43.77 | 58.95 | 44.63 | 51 | 49.98 | 43.04 | 43.51 | 68.48 |
| Total Di-alkyl | 0 | 0.88 | 3.85 | 4.83 | 8.52 | 9.37 | 16.14 | 17.12 | 19.41 | 31.54 |

Example B: alkylation of diphenylamine with 1-octene using Fulcat 220 catalyst 30% by weight. In a 500 mL four-necked round bottom flask equipped with a temperature probe, addition funnel, Dean Stark set up with reflux condenser and overhead stirrer were charged diphenylamine (100 g, 0.585 mole) and clay catalyst Fulcat 220 (30 g). The reaction mixture was rapidly mixed and heated to 130-135° C. under nitrogen. 1-Octene (193 g, 1.685 mole) was added at 135° C. dropwise for two hours. After addition of 1-octene, the reaction mixture was mixed at reflux (135-140° C.) for 25 h. Periodically 1 mL reaction samples were taken for GCMS to check the progress of the reaction. After 25 h, the reaction mixture was cooled to room temperature, and filtered. Excess alkene was distilled off using water aspirator vacuum. A light pink oil (200.18 g) was isolated. GCMS analysis of the various reaction mixtures and final product are provided in Table 2. As the table indicates, all the diphenylamine was reacted after 15 hours and the light pink oil product was composed of 29.86% mono-linear octylated diphenylamine, 63.15% di-linear octylated diphenylamine and 7% tri-linear octylated diphenylamine. This is a desirable product for preparation of triazole derivatives because there is no unreacted diphenylamine in the product.

Example B GCMS timed data: alkylation using Fulcat 220, 30% by weight, 25 h

TABLE 2

| | Time h | | | | | |
|---|---|---|---|---|---|---|
| Chemical | 5 | 10 | 15 | 20 | 25 | dist |
| 1-octene | 1.34 | 6.98 | 7.1 | 8.36 | 8.48 | 0 |
| DPA | 8.38 | 5.28 | 0 | 0 | 0 | 0 |
| Total Mono alkyl | 62.83 | 59.85 | 50.59 | 51.79 | 20.17 | 29.86 |
| Total Di-alkyl | 7.77 | 12.19 | 29.09 | 26.43 | 38.18 | 63.15 |
| Total tri-alkyl | 0 | 0 | 1.45 | 1.4 | 3.3 | 7 |

Example C: alkylation of diphenylamine with 1-octene using Fulcat 220 catalyst 30% by weight. In a 500 mL four-necked round bottom flask equipped with a temperature probe, addition funnel, Dean Stark set up with reflux condenser and overhead stirrer were charged diphenylamine (100 g, 0.585 mole) and clay catalyst Fulcat 220 (30 g). The mixture was heated to 130-135° C. under nitrogen. 1-Octene (193 g, 1.685 mole) was added dropwise for two hours. After addition of 1-octene, the reaction mixture was mixed at reflux (135-140° C.) for 25 h. Periodically, 1 mL reaction samples were taken for GCMS to check the progress of the reaction. After 25 h, the reaction mixture was cooled to room temperature, and filtered. The filtrate was distilled using water aspirator vacuum to remove excess alkene. A dark pink oil (209 g) was isolated. GCMS analysis of the various reaction mixtures and final product are provided in Table 3. As the table indicates, all the diphenylamine was reacted after 20 hours and the dark pink oil product was composed of 50.39% mono-linear octylated diphenylamine, 47.22% di-linear octylated diphenylamine and 2.4% tri-linear octylated diphenylamine. This is a desirable product for preparation of triazole derivatives because there is no unreacted diphenylamine in the product.

Example C GCMS timed data: alkylation using Fulcat 220, 30% by weight, 30 h

TABLE 3

| | Time h | | | | | | |
|---|---|---|---|---|---|---|---|
| Chemical | 5 | 10 | 15 | 20 | 25 | 30 | dist |
| 1-octene | 10.67 | 11.69 | 4.21 | 5.65 | 1.69 | 0 | 0 |
| DPA | 10 | 2.04 | 0.23 | 0 | 0 | 0 | 0 |

TABLE 3-continued

| | Time h | | | | | | |
|---|---|---|---|---|---|---|---|
| Chemical | 5 | 10 | 15 | 20 | 25 | 30 | dist |
| Total Mono alkyl | 68.22 | 61.81 | 64.84 | 43.33 | 40.43 | 24.99 | 50.39 |
| Total Di-alkyl | 5.06 | 9.02 | 11.53 | 18.72 | 21.75 | 24.38 | 47.22 |
| Total tri-alkyl | 0 | 0 | 0 | 0.65 | 1.39 | 1.82 | 2.4 |

Example D: alkylation of diphenylamine with 1-heptene using Fulcat 220 catalyst 30% by weight. In a 500 mL four-necked round bottom flask equipped with a temperature probe, addition funnel, Dean Stark set up with reflux condenser and overhead stirrer were charged diphenylamine (100 g, 0.585 mole) and clay catalyst Fulcat 220 (30 g). The mixture was heated to 95° C. under nitrogen. 1-Heptene (168 g, 1.685 mole) was added dropwise for two hours. After addition of 1-heptene, the reaction mixture was mixed at reflux (95° C.) for 25 h. Periodically, 1 mL reaction samples were taken for GCMS to check the progress of the reaction. After 25 h, the reaction mixture was cooled to room temperature, and filtered. The filtrate was distilled applying water aspirator vacuum to remove excess 1-heptene. A pink solid (113.45 g) was isolated. GCMS analysis of the various reaction mixtures and final product are provided in the table below. As Table 4 indicates, after 25 hours a significant amount of unreacted diphenylamine remained primarily due to the lower reaction temperature caused by the lower boiling point/of 1-heptene compared to 1-octene. Thus, when using the 7-carbon olefin the straightforward process described above for 8 carbon olefins cannot produce the desired product. The solid product was composed of 50.36% unreacted diphenylamine, 49.31% mono-linear heptylated diphenylamine, and only 0.32% di-linear heptylated diphenylamine. Due to the high level of unreacted diphenylamine, this product is undesirable for production of triazole derivatives.

Example D GCMS timed data: alkylation using Fulcat 220, 30% by weight, 25 h 1-heptene

TABLE 4

| | Time h | | | | | |
|---|---|---|---|---|---|---|
| Chemical | 5 | 10 | 15 | 20 | 25 | dist |
| 1-heptene | 0 | 0 | 0 | 0 | 0 | 0 |
| DPA | 98.27 | 96.68 | 85 | 67.09 | 56.62 | 50.36 |
| Total Mono alkyl | 1.73 | 3.32 | 15.01 | 32.9 | 43.21 | 49.31 |
| Total Di-alkyl | 0 | 0 | 0 | 0 | 0.18 | 0.32 |

Preparation of Alkylated Diphenylamine Derivatives of 1,2,4-Triazole

Example 1

Preparation of 1-(N,N-bis(4-(1,1,3,3-tetramethylbutyl)phenyl)aminomethyl)-1,2,4-triazole In a 500 mL three-necked round bottom flask equipped with a temperature probe, overhead stirrer and Dean Stark set up were charged VANLUBE® 81 (dioctylated diphenylamine) (150 g, 0.381 mole), 1,2,4-triazole (26.5 g, 0.383 mole), paraformaldehyde (12.5 g, 0.383 mole) and water (7 g, 0.388 mole). The mixture was heated under nitrogen to 100-105° C. with rapid mixing. Mixing was continued at 100° C. for one hour. After one hour, water aspirator vacuum was applied and the reaction temperature was raised to 120° C. The reaction mixture was held at this temperature for an hour. The expected amount of water was recovered, suggesting a complete reaction occurred. The reaction mixture was allowed to cool to 90° C., and transferred to a container. A light amber oil (175 g) was isolated. $^1$H-NMR CDCl$_3$ δ ppm −0.74 (s, 18H), 1.35 (s, 12H), 1.71 (s, 4H), 6.02 (s, 2H, CH2), 6.99 (d, aromatic, 2H), 7.01 (d, aromatic, 2H), 7.29 (d, aromatic 2H), 7.31 (d, aromatic, 2H), 7.96 (2s, triazole C3 and C5 2H). $^{13}$C-NMR in CDCl$_3$ δ ppm −151.12 (C3 triazole), 144.47 (C5 triazole), 143 (aromatic C), 142.52 (aromatic C), 127 (aromatic CH), 120.28 (aromatic CH), 66.08 (CH2), 55.69 (CH2), 37.79 (tert C), 32.07 (tert C), 31.55 (CH3), 31.26 (CH3).

Example 2

Preparation of Mixed Butylated/Octylated Diphenylamine Derivative of 1,2,4-triazole In a 500 mL three-necked round bottom flask equipped with a temperature probe, overhead stirrer and Dean Stark set up were charged VANLUBE® 961 (mixed butylated/octylated diphenylamine) (150 g, 0.506 mole), 1,2,4-triazole (35 g, 0.506 mole), paraformaldehyde (16.5 g, 0.50 mole) and water (9.3 g, 0.516 mole). The mixture was heated under nitrogen to 100-105° C. with rapid mixing. Mixing was continued at 100° C. for one hour. After one hour, water aspirator vacuum was applied and the reaction temperature was raised to 120° C. The reaction mixture was held at this temperature for an hour. The expected amount of water was recovered, suggesting a complete reaction occurred. The reaction mixture was allowed to cool to 90° C., and transferred to a container. A light amber oil (185.26 g) was isolated.

Example 3

Preparation of Nonylated Diphenylamine Derivative of 1,2,4-triazole

In a 500 mL three-necked round bottom flask equipped with a temperature probe, overhead stirrer and Dean Stark assembly with reflux condenser were charged NAUGA-LUBE® 438L (dinonylated diphenylamine) (200 g, 0.474 mole), 1,2,4-triazole (32.8 g, 0.474 mole), paraformaldehyde (16.3 g, 0.49 mole) and water (9.0 g, 0.49 mole). The mixture was heated under nitrogen to 100-105° C. with rapid mixing. Mixing was continued at 100° C. for one hour. After one hour, water aspirator vacuum was applied and the reaction temperature was raised to 120° C. The reaction mixture was held at this temperature for one hour. The expected amount of water was recovered, suggesting a complete reaction occurred. The reaction mixture was allowed to cool to 90° C., and transferred to a container. A pale pink viscous oil (215.98 g) was isolated.

Example 4A

Triazole Derivative Preparation from Example A Linear Octylated Alkylated Diphenylamine In a 500 mL three-necked round bottom flask equipped with a temperature probe, overhead stirrer and Dean Stark set up were charged the linear octylated diphenylamine from Example A (150 g, 0.535 mole), 1,2,4-triazole (36.8 g, 0.532 mole), paraformaldehyde (18 g, 0.55 mole) and water (9.8 g, 0.544 mole). The mixture was heated under nitrogen to 100-105° C. with rapid mixing. Mixing was continued at 100° C. for one hour. After one hour, water aspirator vacuum was applied and reaction temperature was raised to 120° C. The reaction mixture was held at this temperature for one hour. The expected amount of water was recovered, suggesting a complete reaction occurred. The reaction mixture was allowed to cool to 90° C., and transferred to a container. An amber semi solid-liquid (187.5 g) was isolated.

Example 5B

Triazole Derivative from Example B Linear Octylated Diphenylamine

In a 500 mL three-necked round bottom flask equipped with a temperature probe, overhead stirrer and Dean Stark assembly were charged the linear octylated diphenylamine from Example B (150 g, 0.471 mole), 1,2,4-triazole (33.0 g, 0.477 mole), paraformaldehyde (15.8 g, 0.484 mole) and water (9.0 g, 0.499 mole). The mixture was heated under nitrogen to 100-105° C. with rapid Mixing. Mixing was continued at 100° C. for one hour. After one hour, water aspirator vacuum was applied and reaction temperature was raised to 120° C. The reaction mixture was held at this temperature for one hour. The expected amount of water was recovered, suggesting a complete reaction occurred. The reaction mixture was allowed to cool to 90° C., and transferred to a container. A dark reddish liquid (184.05 g) was isolated.

Example 6C

Triazole Derivative of Example C Linear Octylated Diphenylamine

In a 500 mL three-necked round bottom flask equipped with a temperature probe, overhead stirrer and Dean Stark set up were charged the linear octylated diphenylamine from Example C (150 g, 0.514 mole), 1,2,4-triazole (35.5 g, 0.514 mole), paraformaldehyde (17.2 g, 0.527 mole) and water (9.4 g, 0.522 mole). The mixture was heated under nitrogen to 100-105° C. with rapid mixing. Mixing was continued at 100° C. for one hour. After one hour, water aspirator vacuum was applied and the reaction temperature was raised to 120° C. The reaction mixture was held at this temperature for one hour. The expected amount of water was recovered, suggesting a complete reaction occurred. The reaction mixture was allowed to cool to 90° C., and transferred to a container. A dark reddish liquid (188.52 g) was isolated.

Example 7D

Triazole Derivative of Example D Linear Heptylated Diphenylamine

In a 500 mL three-necked round bottom flask equipped with a temperature probe, overhead stirrer and Dean Stark set up were charged the linear heptylated diphenylamine from Example D (100 g, 0.514 mole), 1,2,4-triazole (35.5 g, 0.514 mole), paraformaldehyde (17.2 g, 0.527 mole) and water (9.4 g, 0.522 mole). The mixture was heated under nitrogen to 100-105° C. with rapid mixing. Mixing was continued at 100° C. for one hour. After one hour, water aspirator vacuum was applied and the temperature was raised to 120° C. The reaction mixture was held at this temperature for one hour. The expected amount of water was recovered, suggesting a complete reaction occurred. The reaction mixture was allowed to cool to 90° C., and transferred to a container. An amber liquid (138.25 g) was isolated.

Volatility Studies on Alkylated Diphenylamines

Figure 2:
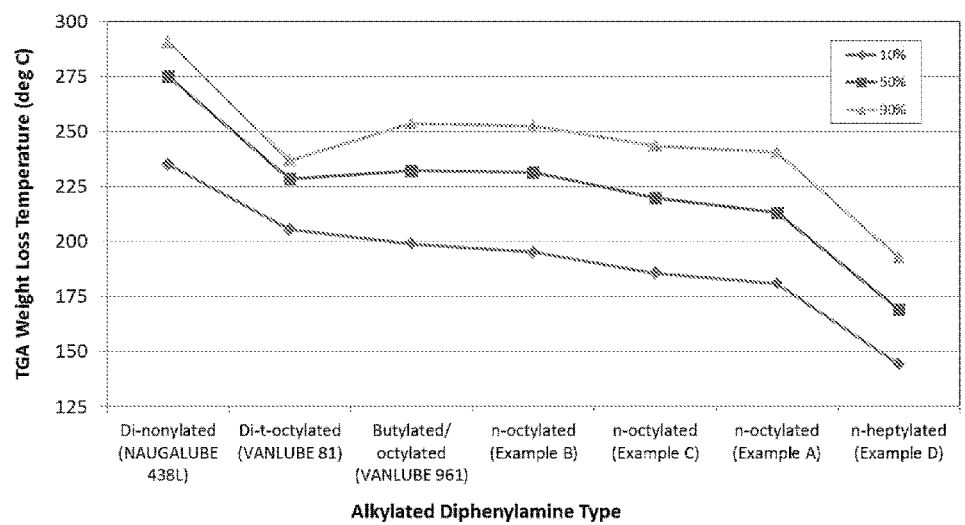
FIG. 2 is a comparative graph showing relative volatility of various alkylated diphenylamines.

A volatility study was performed on the various alkylated diphenylamine samples prepared. Volatility was determined under nitrogen using a TA Instruments Model Q 500 Thermal Gravimetric Analyzer. Sample size was approximately 11 mg for each analysis. Testing was performed with a temperature ramping program of 20° C./minute starting at ambient temperature and ending at 800° C. The samples tested were: Example A, Example B, Example C and Example D. In addition, three commercial alkylated diphenylamine samples were tested: NAUGALUBE® 438L, a commercial nonylated diphenylamine, VANLUBE® 81, a commercial dioctylated diphenylamine, and VANLUBE® 961, a commercial butylated/octylated diphenylamine. The temperature at which a 10% weight loss, 50% weight loss and 90% weight loss of the sample was determined. The results are plotted on the graph in FIG. 2. The results clearly illustrate the significantly reduced volatility of the octylated and nonylated diphenylamines versus the heptylated diphenylamine, making these more favorable additives for lubricants. The high volatility of the heptylated diphenylamine is due to two factors: first, the lower molecular weight of a heptylated product versus the octylated and nonylated products; and second, the significantly poorer reactivity of a heptene based olefin to produce an alkylated product caused by its much lower boiling point compared to octene and nonene type olefins. Thus heptylated diphenylamines are inherently more difficult to prepare and have considerably higher volatility.

Volatility Studies on Alkylated Diphenylamine Derivatives of 1,2,4-Triazole

Figure 3:
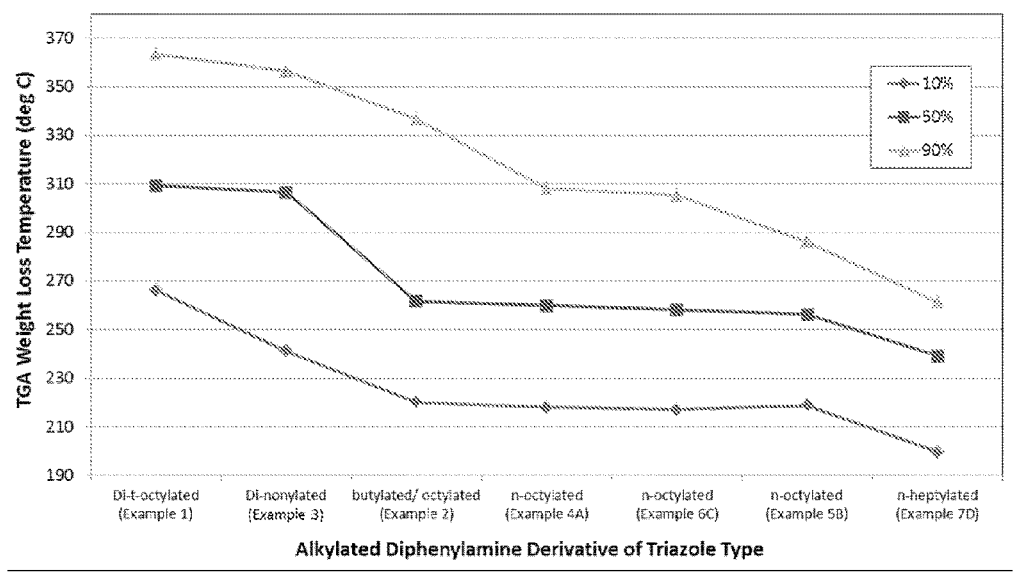
FIG. 3 is a comparative graph showing relative volatility of various alkylated diphenylamine derivatives of triazole.

A volatility study was performed on the various alkylated diphenylamine derivatives of triazoles. Volatility was determined under nitrogen using a TA Instruments Model Q 500 Thermal Gravimetric Analyzer. Sample size was approximately 11 mg for each analysis. Testing was performed with a temperature ramping program of 20° C./minute starting at ambient temperature and ending at 800° C. The samples tested were: Example 1, Example 2, Example 3, Example 4A, Example 5B, Example 6C and Example 7D. The temperature at which a 10% weight loss, 50% weight loss and 90% weight loss of the sample was determined. The results are plotted on the graph in FIG. 3. The results clearly illustrate the significantly reduced volatility of the octylated and nonylated diphenylamine derivatives of triazole versus the heptylated diphenylamine derivative of triazole, making these more favorable additives for lubricants. The high volatility of the heptylated diphenylamine derivative of triazole is due to two factors: first, the lower molecular weight of a heptylated product versus the octylated and nonylated products; and second, the significantly poorer reactivity of a heptene based olefin to produce an alkylated product caused by it's much lower boiling point compared to octene and nonene type olefins. Thus heptylated diphenylamine derivatives of triazole are inherently more difficult to prepare and have considerably higher volatility.

Preparation of Alkylated Diphenylamine Derivatives of Triazole in a Synthetic Ester Diluent.

Example 8

Preparation of 1-[di-(4-octylphenyl)aminomethyl] triazole in Synthetic Ester

HATCOL® 2965 synthetic ester oil (47.8 g), 1,2,4-Triazole (7.0 g), 4,4'-di-octyldiphenylamine (VANLUBE® 81, 39.3 g), and paraformaldehyde (3.0 g) were added to a 500-ml, 3-neck reaction flask, which was fitted with temperature controller, agitator and condenser. The mixture was preheated to 120° C. for 1 hour to create a uniform solution. Subsequently the reaction temperature was raised to 125° C. and aspirator vacuum was applied onto the flask. The reaction was held at 125° C. for 3 hours. The reaction product was filtered at 120° C. upon completing the reaction. The resulting product contained approximately 50% HATCOL® synthetic diluent oil and had a nitrogen content of 5.6 wt. %.

Example 9

Preparation of 1-[di-(4-mixed butyl/octylphenyl)aminomethyl]triazole in Synthetic Ester HATCOL® 2965 synthetic ester oil (40.7 g), 1,2,4-Triazole (7.3 g), butylated octylated diphenylamine (VANLUBE® 961, 32.2 g), and paraformaldehyde (3.0 g) were added to a 500-ml, 3-neck reaction flask, which was fitted with temperature controller, agitator and condenser. The mixture was preheated to 120° C. for 1 hour to create a uniform solution. Subsequently the reaction temperature was raised to 125° C. and aspirator vacuum was applied onto the flask. The reaction was held at 125° C. for 3 hours. The reaction product was filtered at 120° C. upon completing the reaction. The resulting product contained approximately 50% HATCOL® synthetic diluent oil and had a nitrogen content of 6.9 wt. %.

Preparation of Alkylated Diphenylamine Derivatives of Triazole in a Process Oil Diluent.

Example 10

Preparation of 1-(N,N-bis(4-(1,1,3,3-tetramethylbutyl)phenyl)aminomethyl)-1,2,4-triazole in 50% Process Oil In a 500 mL three-necked round bottom flask equipped with a temperature probe, overhead stirrer and Dean Stark set up were charged VANLUBE® 81 (dioctyl diphenylamine) (62.5 g, 0.158 mole), 1,2,4-triazole (11.0 g, 0.158 mole), paraformaldehyde (5.5 g, 0.158 mole), water (3 g, 0.166 mole) and process oil (37.7 g). The mixture was heated under nitrogen to 100-105° C. with rapid mixing. Mixing was continued at 100° C. for one hour. After one hour, water aspirator vacuum was applied and the reaction temperature was raised to 120° C. The reaction mixture was held at this temperature for an hour. The expected amount of water was recovered, suggesting a complete reaction occurred. The reaction mixture was allowed to cool to 90° C., and transferred to a container. A light amber liquid (102.93 g) was isolated.

Example 11

Preparation of Mixed Butylated/Octylated Diphenylamine Derivative of 1,2,4-triazole in 50% Process Oil In a 500 mL three-necked round bottom flask equipped with a temperature probe, overhead stirrer and Dean Stark set up were charged VANLUBE® 961 (mixed butylated/octylated diphenylamine) (60 g, 0.201 mole), 1,2,4-triazole (13.9 g, 0.200 mole), paraformaldehyde (6.8 g, 0.207 mole), water (3.8 g, 0.208 mole) and process oil (77 g). The mixture was heated under nitrogen to 100-105° C. with rapid mixing. Mixing was continued at 100° C. for one hour. After one hour, water aspirator vacuum was applied and the reaction temperature was raised to 120° C. The reaction mixture was held at this temperature for an hour. The expected amount of water was recovered, suggesting a complete reaction occurred. The reaction mixture was allowed to cool to 90° C., and transferred to a container. A dark amber liquid (138.86 g) was isolated.

Example 12 (Comparative)

Preparation of 1-[di(4-octylphenyl)aminomethyl] tolutriazole

In a 500 mL three-necked round bottom flask equipped with a temperature probe, overhead stirrer and Dean Stark set up were charged VANLUBE® 81 (190.0 g, 0.482 mole), tolutriazole (65.0 g, 0.488 mole), paraformaldehyde (15.7 g, 0.481 mole) and water (8.7 g, 0.483 mole). The mixture was heated under nitrogen to 100-105° C. with rapid mixing. Mixing was continued at 100° C. for one hour. After one hour, water aspirator vacuum was applied and the reaction temperature was raised to 120° C. The reaction mixture was held at this temperature for an hour. The expected amount of water was recovered, suggesting a complete reaction occurred. The reaction mixture was allowed to cool to 90° C., and transferred to a container. A light oil which crystallized to a solid mass at room temperature (265.62 g) was isolated.

Physical Form of Alkylated Diphenylamine Derivatives of Triazole

The following samples were observed over a prolonged period of time for haze formation, crystallization or fall out. The results are tabulated in Table 5. The results clearly show that alkylated diphenylamine derivatives of triazole remain clear liquids or clear oils under prolonged storage conditions. However, the analogous alkylated diphenylamine derivatives of tolutriazole are solids in the neat form or readily form crystals when diluted in 50% process oil.

TABLE 5

| Sample | Description | Dilution | Initial Appearance | Storage Time | Appearance After Storage |
| --- | --- | --- | --- | --- | --- |
| Example 8 | t-octylated diphenylamine derivative of triazole | 50% in ester | Clear brown liquid | 24 months | Clear brown liquid |
| Example 9 | Mixed t-butylated/t-octylated diphenylamine derivative of triazole | 50% in ester | Clear dark brown liquid | 24 months | Clear dark brown liquid |
| Example 10 | t-octylated diphenylamine derivative of triazole | 50% in process oil | Clear light brown liquid | 4 months | Clear light brown liquid |

TABLE 5-continued

| Sample | Description | Dilution | Initial Appearance | Storage Time | Appearance After Storage |
|---|---|---|---|---|---|
| Example 11 | Mixed t-butylated/t-octylated diphenylamine derivative of triazole | 50% in process oil | Clear brown liquid | 4 months | Clear brown liquid |
| Example 2 | Mixed t-butylated/t-octylated diphenylamine derivative of triazole | None (neat) | Clear dark brown viscous oil | 4 months | Clear dark brown viscous oil |
| Example 1 | t-octylated diphenylamine derivative of triazole | None (neat) | Clear brown oil | 4 months | Clear brown oil |
| Example 3 | Nonylated diphenylamine derivative of triazole | None (neat) | Clear yellow viscous oil | 3 months | Clear yellow viscous oil |
| Example 12 (comparator) | t-octylated diphenylamine derivative of tolutriazole | None (neat) | Solid | 3 months | Solid |
| VANLUBE ® 887 (comparator) | t-octylated diphenylamine derivative of tolutriazole | 50% in process oil | Clear light amber liquid | Commercial product readily forms crystals on storage for short periods of time | |

Antioxidant Evaluation of Alkylated Diphenylamine Derivatives of Triazole and Comparison with Alkylated Diphenylamine Derivatives of Tolutriazole The Rotating Pressure Vessel Oxidation Test (RPVOT, ASTM D 2272) is a turbine oil oxidation test used as a quality control tool for new and used turbine oils of known composition, as well as a research tool for estimating the oxidative stability of experimental oils. The test evaluates the oxidative stability of turbine oil at elevated temperatures and oxygen pressures and in the presence of a copper coil oxidation catalyst and water. A rotating glass pressure vessel provides maximum oil-oxygen contact. Results are reported as the time to a 25 psi drop in oxygen pressure. The test oil, copper coil and water are placed in the glass oxidation pressure vessel. The vessel is sealed and pressurized to 90 psi of oxygen. The pressurized vessel is placed in a high temperature bath maintained at 150° C. and continuously rotated throughout the test period. The test is monitored for consumption of oxygen. The time from the start of the test to the point when the pressure of the vessel has dropped 25 psi is defined as the oxidation life or oxidation induction time.

FIG. 1: In FIG. 1, it can be seen that the expected antioxidant effect based on the addition of the DTC falls along the straight dotted line. While the synergistic effect in terms of antioxidation does indeed fall above the ratio of 1:1, it is surprising that the synergistic antioxidant effect is significantly greater with the triazole derivative compared to the tolutriazole derivative. Also, the antioxidant synergistic effect in the range tested in U.S. Pat. No. 6,743,759 is much greater when the triazole derivative {1-[di(4-octylphenyl)aminomethyl]triazole} is used compared to the tolutriazole derivative {1-[di(4-octylphenyl)aminomethyl]tolutriazole}. Note in FIG. 1:

1) the dashed line with triangle points are estimated results taken directly from FIG. 1 in U.S. Pat. No. 6,743,759.
2) The dashed line with square points are retested results under the same conditions as reported in U.S. Pat. No. 6,743,759.
3) The solid line with diamond points replace 1-[di(4-octylphenyl)aminomethyl]tolutriazole with 1-[di(4-octylphenyl)aminomethyl]triazole and represent the invention.

With references to Table 6 below, blends A-P were prepared by adding an appropriate amount of methylenebis(di-n-butyldithiocarbamate)—"DTC" and 1-[di(4-octylphenyl)aminomethyl]tolutriazole—"tolutriazole derivative" or 1-[di(4-octylphenyl)aminomethyl]triazole—"triazole derivative" to a base oil (Exxon 150 manufactured by ExxonMobil Corp.). The ratios of methylenebis(di-n-butyldithiocarbamate):1-[di(4-octylphenyl)aminomethyl]tolutriazole or triazole [(a):(b)] were intended to duplicate specific points defined in U.S. Pat. No. 6,743,759; Blend A (comparative example) and Blend E (inventive example) provide an (a):(b) ratio of 5.73; Blend B (comparative example) and Blend F (inventive example) provide an (a):(b) ratio of 11.5; Blend C (comparative example) and Blend G (inventive example) provide an (a):(b) ratio of 19.2; Blend D (comparative example) and Blend H (inventive example) provide an (a):(b) ratio of 1.0. As can be seen in all cases the inventive blends with the triazole derivative perform significantly better than the comparative blends with the tolutriazole derivative.

Blends I-K show the individual additive response for DTC, the tolutriazole derivative and the triazole derivative.

Blends L-O show the effect when the 1-[di(4-octylphenyl)aminomethyl]triazole is replaced with a 1-[di(2-ethylhexyl)aminomethyl]triazole, a structurally different triazole derivative. The results show that in all cases no synergistic effect is observed. Note the treat rate of 1-[di(2-ethylhexyl)aminomethyl]triazole is corrected to account for a different activity (or nitrogen content) level.

Blend P shows the individual additive response for 1-[di(2-ethylhexyl)aminomethyl] triazole.

TABLE 6

| Blends | Type | A | B | C | D | E | F | G | H |
|---|---|---|---|---|---|---|---|---|---|
| (a) VANLUBE ® 7723 | methylenebis(dibutyldithiocarbamate) | 0.43 | 0.46 | 0.48 | 0.25 | 0.43 | 0.46 | 0.48 | 0.25 |
| VANLUBE ® 887E (5.4%) | 1-[di-(4-octylphenyl)aminomethyl]tolutriazole (in 50% synthetic ester) | 0.15 | 0.081 | 0.05 | 0.5 | | | | |
| (b)VANLUBE ® 887E (5.4%) | 1-[di-(4-octylphenyl)aminomethyl]tolutriazole (excluding synthetic ester weight) | 0.075 | 0.04 | 0.025 | 0.25 | | | | |

TABLE 6-continued

| Example 8(5.6%) | 1-[di-(4-octylphenyl)aminomethyl]triazole (in 50% synthetic ester) | | | | | 0.15 | 0.081 | 0.05 | 0.5 |
| --- | --- | --- | --- | --- | --- | --- | --- | --- | --- |
| (b) Example 8 (5.6%) | 1-[di-(4-octylphenyl)aminomethyl]triazole (excluding synthetic ester weight) | | | | | 0.075 | 0.04 | 0.025 | 0.25 |
| IRGAMET ® 30 (17.4%) | 1-[di-(2-ethylhexyl)aminomethyl]triazole | | | | | | | | |
| Exxon ® 150 SN | Group 1 base oil | 99.42 | 99.46 | 99.47 | 99.25 | 99.42 | 99.46 | 99.47 | 99.25 |
| Mass ratio (a):(b) | | 5.73 | 11.5 | 19.2 | 1.0 | 5.73 | 11.5 | 19.2 | 1.0 |
| Total (a) + (b) | | 0.51 | 0.5 | 0.51 | 0.5 | 0.51 | 0.5 | 0.51 | 0.5 |
| Total | | 100 | 100 | 100 | 100 | 100 | 100 | 100 | 100 |
| Appearance @RT | | | | | | | | | |
| RPVOT | | | | | | | | | |
| Test 1 | minutes | 901 | 506 | 391 | 1122 | 1138 | 893 | 544 | 1422 |
| Test 2 | minutes | 973 | 573 | 367 | 1025 | 1103 | 1038 | 693 | 1079 |
| Test 3 | minutes | | | | 1147 | 1280 | 924 | | |
| Average | minutes | 937 | 540 | 379 | 1098 | 1234 | 952 | 619 | 1251 |

| Blends | Type | I | J | K | L | M | N | O | P |
| --- | --- | --- | --- | --- | --- | --- | --- | --- | --- |
| (a) VANLUBE ® 7723 | methylenebis(dibutyldithiocarbamate) | 0.5 | | | 0.43 | 0.46 | 0.48 | 0.25 | |
| VANLUBE ® 887E (5.4%) | 1-[di-(4-octylphenyl)aminomethyl]tolutriazole (in 50% synthetic ester) | | 1 | | | | | | |
| VANLUBE ® 887E (5.4%) | 1-[di-(4-octylphenyl)aminomethyl]tolutriazole (excluding synthetic esterI weight) | | | 0.5 | | | | | |
| Example 8 (5.6%) | 1-[di-(4-octylphenyl)aminomethyl]triazole (in 50% synthetic ester) | | | | 1 | | | | |
| Example 8 (5.6%) | 1-[di-(4-octylphenyl)aminomethyl]triazole (excluding synthetic esterweight) | | | | 0.5 | | | | |
| (b) IRGAMET ® 30 (17.4%) | 1-[di-(2-ethylhexyl)aminomethyl]triazole | | | | 0.048 | 0.026 | 0.016 | 0.161 | 0.322 |
| Exxon ® 150 SN | Group 1 base oil | 99.5 | 99 | 99 | 99.522 | 99.514 | 99.504 | 99.589 | 99.678 |
| Mass ratio (a):(b) | | | | | 8.96 | 17.7 | 30 | 1.55 | |
| Total (a) + (b) | | | | | 0.48 | 0.49 | 0.50 | 0.41 | |
| Total | | 100 | 100 | 100 | 100 | 100 | 100 | 100 | 100 |
| Appearance @RT | | | | | | | | | |
| RPVOT | | | | | | | | | |
| Test 1 | minutes | 31 | 1057 | 1035 | 55.5 | 58 | 57 | 55 | 48.5 |
| Test 2 | minutes | 35 | 1003 | 779 | | | | | |
| Test 3 | minutes | | 980 | | | | | | |
| Average | minutes | 33 | 1013 | 922 | 55.5 | 58 | 57 | 55 | 48.5 |

The above embodiments have shown various aspects of the present invention. Other variations will be evident to those skilled in the art. Such modifications are intended to be within the scope of the invention as defined by the amended claims.

What is claimed is:

1. A lubricating composition comprising a major amount of a base oil and an antioxidant composition which comprises:
   (a) methylenebis(di-n-butyldithiocarbamate); and
   (b) an alkylated diphenylamine derivative of 1,2,4-triazole being 1-[di-(4-octylphenyl)aminomethyl]triazole,
   wherein the antioxidative composition is present in an amount from about 0.5 to about 1.0% by weight, based on the total weight of the lubricating composition, wherein the (a):(b) mass percent ratio ranges from above about 1:1 to about 20:1.

2. The lubricating composition of claim 1, wherein the composition is substantially free of alkylated phenyl-α-naphthylamine (APANA).

3. A lubricating composition comprising a major amount of a base oil and an antioxidant composition which comprises:
   (a) methylenebis(di-n-butyldithiocarbamate); and
   (b) an alkylated diphenylamine derivative of 1,2,4-triazole being 1-[di-(4-mixed butyl/octylphenyl)aminomethyl]triazole,
   wherein the antioxidative composition is present in an amount from about 0.5 to about 1.0% by weight, based on the total weight of the lubricating composition, wherein the (a):(b) mass percent ratio ranges from above about 5.7:1 to about 9:1.

4. The lubricating composition of claim 3, wherein the composition is substantially free of alkylated phenyl-α-naphthylamine (APANA).

* * * * *